US010619129B2

(12) United States Patent
Cesana et al.

(10) Patent No.: US 10,619,129 B2
(45) Date of Patent: Apr. 14, 2020

(54) METHOD FOR HUMIDIFYING AN INCUBATOR, AND INCUBATOR (71) Applicant: ADOLF KÜHNER AG, Birsfelden (CH)

(72) Inventors: Christoph Cesana, Basel (CH); Joan Batlle, Baselstadt (CH); Tim Bürgin, Liestal (CH); Simon Knobel, Pratteln (CH); Tibor Anderlei, Müllheim (DE); Mathias Schumacher, Lörrach (DE)

(73) Assignee: ADOLF KÜHNER AG, Birsfelden (CH)

(*) Notice: Subject to any disclaimer, the term of this patent is extended or adjusted under 35 U.S.C. 154(b) by 131 days.

(21) Appl. No.: 15/910,555

(22) Filed: Mar. 2, 2018

(65) Prior Publication Data

US 2018/0251720 A1 Sep. 6, 2018

(30) Foreign Application Priority Data

Mar. 3, 2017 (DE) .................. 10 2017 104 508

(51) Int. Cl.
*F24F 6/02* (2006.01)
*C12M 1/00* (2006.01)
(Continued)

(52) U.S. Cl.
CPC .............. *C12M 41/14* (2013.01); *B01L 7/00* (2013.01); *C12M 1/38* (2013.01); *C12M 41/00* (2013.01);
(Continued)

(58) Field of Classification Search
CPC ...... C12M 41/04; F24F 6/025; F24F 11/0008; B01L 2300/10; B01L 2300/1805
See application file for complete search history.

(56) References Cited

U.S. PATENT DOCUMENTS 5,546,926 A * 8/1996 Lake .................. F24F 6/02
126/113
2011/0189765 A1 8/2011 Fukui et al.
(Continued)

FOREIGN PATENT DOCUMENTS

DE 3630886 C1 12/1987
DE 202007005865 U1 7/2007
(Continued)

OTHER PUBLICATIONS www.kuhner.com/de/produkte/schuettelmaschinen/inkubatoren/lsf1-xhtml, downloaded on Feb. 13, 2017.

*Primary Examiner* — Marc E Norman
(74) *Attorney, Agent, or Firm* — Lucas & Mercanti, LLP (57) ABSTRACT A method for the regulated humidification and temperature control of a gas mixture in an inner chamber of an incubator, which inner chamber is sealed off from the surroundings by a housing, includes conducting heat from at least one condensation surface inside the incubator, which at least one condensation surface is separate from the inner surfaces of the inner chamber, is conducted out of the incubator to the outside through a wall delimiting the inner chamber by a heat conductor. Outside the incubator, the heat conductor is connected to a cooling body which releases the heat to the relatively cold ambient air. The method allows dispensing with a cooling unit and at the same time avoid sources of contamination due to moisture condensing out.

23 Claims, 4 Drawing Sheets

(51) Int. Cl.
    *C12M 1/38*     (2006.01)
    *C12M 1/34*     (2006.01)
    *B01L 7/00*     (2006.01)
    *F24F 11/00*     (2018.01)

(52) U.S. Cl.
    CPC ............ *C12M 41/34* (2013.01); *C12M 41/44* (2013.01); *F24F 6/025* (2013.01); *F24F 11/0008* (2013.01); *B01L 2200/0678* (2013.01); *B01L 2300/0627* (2013.01); *B01L 2300/10* (2013.01); *B01L 2300/1805* (2013.01); *B01L 2300/1844* (2013.01); *B01L 2300/1883* (2013.01); *B01L 2300/1894* (2013.01)

(56) References Cited

U.S. PATENT DOCUMENTS

2014/0356934 A1     12/2014     Barka et al.
2016/0010049 A1*     1/2016     Tokumaru .............. C12M 41/14
                                                                           435/303.1
2016/0215252 A1     7/2016     Nishimura et al.

FOREIGN PATENT DOCUMENTS

| DE | 102006022652 B4 | 6/2008 |
|---|---|---|
| DE | 102013009136 A1 | 12/2014 |
| EP | 2573162 A1 | 3/2013 |
| EP | 2963105 A1 | 1/2016 |
| JP | H07318268 A | 12/1995 |

\* cited by examiner

METHOD FOR HUMIDIFYING AN INCUBATOR, AND INCUBATOR

CROSS-REFERENCE TO RELATED APPLICATIONS

The present invention claims priority to DE 10 2017 104 508.2, filed on Mar. 3, 2017, which is incorporated herein by reference.

BACKGROUND OF THE INVENTION

The invention relates to a method for the regulated humidification and temperature control of a gas mixture in an inner chamber of an incubator, in which the inner chamber is sealed off from the surroundings by a housing.

The invention also relates to an incubator with regulated humidification and temperature control of a gas mixture in an inner chamber which is sealed off.

Incubators serve for storing samples in their inner chamber under predefined conditions, such as a certain temperature and air humidity, and in a defined gas atmosphere. A typical inner chamber temperature varies in a range of 20-40 degrees Celsius at a humidity of the gas mixture in the inner chamber in the range of 70-90%. Furthermore, so-called "shaking incubators" are known, which provide ideal conditions for cultivation processes.

Moisture regulation in incubators, in particular shaking incubators, is important to reduce evaporation, in particular in the case of long-lasting cultivations of up to 14 days and very small culture liquid volumes, in particular in microtiter plates. High evaporation leads to a change of the cultivation medium and influences the growth and the metabolism of the cells.

A reduction in the evaporation is achieved by humidification of the gas mixture in the inner chamber of the incubator. Here, the principle applies that the higher the humidity of the gas mixture in the inner chamber, the lower the evaporation of the culture medium. However, at very high humidity values of over 85%, there is the risk of moisture condensing out on inner surfaces of the incubator because of the temperature distribution not being completely homogeneous. Such moisture regions which form as a result of the condensing out constitute potential sources of contamination.

DE 10 2006 022 652 B4 discloses a shaker incubator and a method for the humidification and temperature control of the air in the inner chamber of the incubator, in which moisture is fed to the air from a moisture source of a humidification device, and the temperature of the air is controlled via an incubator heater and/or incubator cooler. As a result of two air circuits which are separate from one another, the humidity of the air in the inner chamber can be regulated using a conventional humidification device almost independently of the temperature regulation with the aid of the incubator heater and/or cooler. Use is made of a temperature-regulated water bath as a humidification device in a known way. The humidity in the inner chamber is measured by a humidity sensor. The regulation of the moisture is realized by regulation of the air stream in the first air circuit, which has the humidification device, and by regulation of the heating element of the water bath.

It is not possible to actively reduce the humidity by the known incubator and the method for the regulated humidification and temperature control of the air in the inner chamber of the incubator. For this purpose, moisture has to be removed from the air.

Adolf Kühner AG Dinkelbergstr. 1, 4127 BIRSFELDEN (Basel), Switzerland produces shaker incubators with an optional humidity regulator, inter alia under the designation ISF1-X. In order to increase the humidity of the gas mixture, a water bath is arranged in the inner chamber of the incubator. The temperature in the water bath is increased by an electric heater and increases the humidity of the gas mixture in the inner chamber by evaporation of the water. To actively reduce the humidity, a cooling circuit of a compressor cooler is integrated into the incubator. The evaporator of the cooling circuit is situated in the inner chamber as a condensation surface. The moist gas mixture condenses on the evaporator which is provided such that the condensed water drips or flows back into the water bath. The regulation is realized with the aid of a capacitive sensor for measuring the actual value of the humidity of the gas mixture in the inner chamber. A digital PID regulator increases the humidity by evaporation of water from the electrically heated water bath if, because of the continuous reduction in the humidity at the evaporator, the actual value is less than the target value. The continuous heat dissipation at the evaporator is maintained by controlling the temperature of the gas mixture to a desired value of the inner chamber temperature by a heater (www.kuhner.com/de/produkte/schuettel-maschinen/inkubatoren/isf1-xhtml, downloaded on 13.02.2017).

In the incubator ISF1-X of the company Kühner AG, the compressor cooler performs two tasks. It can lower the inner chamber temperature and reduce the humidity of the gas mixture in the inner chamber. However, incubators, in particular shaking incubators, are often operated at a constant inner chamber temperature in a range of 32-37 degrees Celsius by their users so that lowering of the inner chamber temperature is not necessary. But, the cooling unit is necessary for the humidity regulation.

BRIEF SUMMARY OF THE INVENTION

Proceeding from this prior art, an object of the present invention is to provide a method for the regulated humidification and temperature control of a gas mixture in an inner chamber of an incubator, which inner chamber is sealed off from the surroundings by a housing, the method requiring no cooling unit and at the same time avoiding sources of contamination due to moisture condensing out. A further object of the invention is to provide an incubator for carrying out the method.

The object of the present invention is met by a method in which heat is conducted from at least one condensation surface inside the incubator out of the incubator to the outside through a wall delimiting the inner chamber by at least one heat conductor. Outside of the incubator, each heat conductor is connected to a cooling body which releases the heat to the relatively cold ambient air.

The solution according to the present invention is less expensive than the known solution having a cooling unit. Added to this is the robustness due to the simple design. As a result of the arrangement of the cooling body outside the housing as a separate component, the solution according to the invention can be retrofitted to existing incubators without any problems.

In particular, it is possible for cooling units with climate-damaging refrigerants to be removed at the request of the customer and replaced by the solution according to the present invention.

In order to improve the heat transfer from the cooling body to the ambient air, the active surface of the cooling body may be profiled. For example, the profiled cooling body may have multiple lamellae which are arranged parallel to one another. In order to keep the heat resistance of the cooling body low, it preferably consists of material with good heat conductivity, such as for example copper or aluminum. The surface of the cooling body is preferably provided with a corrosion-resistant, anti-adhesive and wear-resistant layer. Consequently, protection of the surface against damage, corrosion and environmental influences is provided. The cooling body is designed as a component separate from the housing and is preferably fastened to one of the side walls of the housing of the incubator.

To connect the cooling body to the at least one heat conductor, the cooling body preferably has a plate-like solid component with an opening for receiving one end of each heat conductor in a form-fitting manner. The plate-like component likewise consists of a material with good heat conductivity, in particular of aluminum or copper. The plate-like component is preferably screwed to a wall of the housing of the incubator. Flanges which laterally adjoin the plate-like component may be provided for the purpose of screwing.

To transfer the heat from the condensation surface to the cooling body, use is made of at least one heat conductor.

The heat conductors are for example rods composed of material with good heat conductivity, such as for example aluminum or copper. In a particularly preferred embodiment of the present invention, the heat conductor is a heat pipe. A major advantage of the heat pipe is that its heat resistance, at working temperature, is significantly lower than the heat resistance of metals. At an equal heat transfer capacity, a more compact construction than in the case of conventional heat conductors composed of metal is therefore possible when heat pipes are used. To avoid heat losses and condensate formation on that section of the heat conductor which runs in the inner chamber during the transfer of the heat from the condensation surface to the cooling body arranged outside the housing, the conductor is provided with heat insulation in an advantageous configuration of the invention. In the longitudinal direction, the heat insulation preferably extends over the entire length of the heat conductor with the exception of the ends via which the heat is introduced or transferred to the cooling body. In particular, the heat insulation surrounds each heat conductor even in the region of the passage openings in the housing wall, with the result that only the desired cold bridge, produced by the heat conductor, to the cooling body is formed. The insulation surrounding the heat conductor abuts in a flush manner against the surfaces delimiting the exit openings. Cooling of the housing wall and unwanted condensation on an inner surface of the housing wall which results therefrom are avoided.

The temperature control of the gas mixture to an inner chamber temperature which is constant for technical purposes, typically in the range of 32-37 degrees Celsius (cultivation temperature), is realized by regulated heating. To ensure a uniform temperature distribution in the inner chamber, the walls of the incubator including the closeable opening, in particular of the door, may be provided with wall heating elements. This results in unwanted contamination by condensation of moisture on partial regions of the walls and/or of the door being avoided.

For the purpose of humidification regulation, the incubator has a humidification device whose evaporative capacity is settable. Heatable liquid baths, in particular water baths, ultrasonic evaporators and heated plates onto which liquid drips may in principle be taken into consideration as a humidification device. In a preferred embodiment of the incubator, the humidification device has a container which is arranged in the inner chamber and which serves for holding the liquid to be evaporated. The container has at least one opening which exposes the surface of the liquid. Preferably, the entire top side of the container is open, with the result that the container constitutes a trough or shell. The container also has a heater for feeding thermal energy into the liquid. The heater comprises one or more heating elements which on the outer side of the container or which dip into the liquid.

Preferably, the heatable liquid bath is arranged directly in the inner chamber of the incubator on the bottom surface thereof, but not in any gas-guiding ducts of the inner chamber. The container for holding the liquid bath is easily accessible as a result of said arrangement and can be cleaned and/or removed and cleaned without any problems. Contamination due to bacterially contaminated liquid in the container can thereby be avoided. In particular, this open arrangement of the container permits an advantageous arrangement of the condensation surface(s).

In the first embodiment of the invention, it is expedient if the heat conductors consist of multiple constituent parts which are releasably connected to one another. For the cleaning of the container, the heat transfer body and those sections of each heat conductor which project into the container can be dismounted without any problems.

In order to reduce the humidity of the gas mixture by condensation, at least one condensation surface is arranged in the inner chamber. The condensation surface is a defined surface which is different from the inner surfaces of the housing. Due to the separation of the condensation surface from the housing, it is possible for uncontrolled condensation and accumulations of condensed water to be avoided in the housing.

Contamination of the inner chamber of the incubator by condensing moisture is avoided particularly effectively in an embodiment of the present invention in that the moisture of the gas mixture condenses on the surface of the liquid in the container, which surface at the same time forms the condensation surface. The heat is transferred from the liquid surface to the cooling body arranged outside the housing with the aid of the at least one heat conductor. For this purpose, an end of each heat conductor which is remote from the cooling body dips into the liquid. To improve the heat transfer, the end of the at least one heat conductor is connected in a heat-conducting manner to a heat exchange body, wherein the heat exchange body dips at least partially, but preferably completely, into the liquid. The heat exchange body likewise consists of a material with good heat conductivity, such as for example copper or aluminum.

In a preferred embodiment, the heat exchange body is arranged in such proximity to the bottom of the container that the heat exchange body is still completely covered by liquid in the case of a lowest liquid level in the container being reached. Starting from the heat exchange body, each heat conductor may be led out of the container via the water surface through the opening exposing the surface. Alternatively, it is possible for the heat conductor to be led out through a wall of the container.

In a second embodiment of the invention, the moisture condenses on the surface of a heat exchange body which is separate from the incubator housing and which is arranged in the inner chamber of the incubator. In this case, the surface of the heat exchange body forms the condensation surface. The heat exchange body consists of material with good heat conductivity, such as for example copper or aluminum. Connected to the heat exchange body is the at least one heat conductor for transferring the heat from the heat exchange body to the cooling body arranged outside the housing.

In order to enlarge the condensation surface formed by the heat exchange body, the heat exchange body may be structured, for example by lamellae which are arranged parallel to one another. In order to avoid contamination of the inner chamber as a result of moisture condensing on the heat exchange body, the heat exchange body is arranged above the at least one opening in the container such that the condensate flows or drips directly into the liquid container arranged below the heat exchange body.

In both embodiments of the incubator according to the present invention, the heat transfer from the cooling body to the ambient air is able to be varied by varying the flow of the ambient air along the heat-emitting surfaces of the cooling body by at least one fan. The fan is for example an axial fan whose axis of rotation is substantially perpendicular to the wall to which the cooling body is fastened. The fan is expediently fastened to the cooling body, with the result that the cooling body and the at least one fan form a structural unit.

The fan may be integrated into the humidity regulation so that the air throughput through the cooling body is able to be reduced if required. A reduction in the air throughput allows the continuous transfer of heat to the cooling body to be reduced, with the result that low evaporative capacity is required in the case of high target values for the humidity of the gas mixture. In particular, the fan(s) may be switched off or have their rotational speed reduced to achieve high target values of the humidity of the gas mixture.

To ensure a uniform distribution of temperature and humidity in the inner chamber of the incubator, the gas mixture in the inner chamber is continuously circulated. The circulation is realized in particular by at least one fan arranged in the inner chamber. The fan is designed for example as an axial fan which is fastened to the top of the incubator.

The humidity regulator of the incubator includes at least one humidity sensor arranged in the inner chamber of the housing and which serves for the measurement of the humidity of the gas mixture in the inner chamber. This is in particular a capacitive sensor whose electrical capacity varies with the humidity. The humidity sensor measures the actual humidity, that is to say the actual value of the gas mixture in the housing.

The humidity regulator regulates the humidity of the gas mixture in the inner chamber of the incubator to a settable, substantially constant target value. The humidity regulator, which is designed for example as a PID regulator, compares the actual value with the target value for the humidity.

If there is a deviation of the actual value from the target value, in the first embodiment of the invention, the evaporative capacity is regulated by the heater such that no moisture condenses on the liquid surface, and liquid evaporates, until the target value of the humidity is reached if the measured actual value is less than the target value (the feeding of thermal energy to the liquid in the container predominates over the continuous withdrawal of energy to the cooling body by the at least one heat conductor, with the result that liquid can evaporate from the container), or moisture condenses on the liquid surface, and no liquid evaporates, until the target value of the humidity is reached if the measured actual value is greater than the target value (the feeding of thermal energy to the liquid in the container is sufficiently restricted, or completely prevented, so that the continuous withdrawal of energy from the liquid bath to the cooling body by the at least one heat conductor leads to such intense cooling of the liquid surface that the moisture condenses on the liquid surface).

If there is a deviation of the actual value from the target value, in the second embodiment of the invention, the evaporative capacity is regulated by the heater such that liquid evaporates, to a large extent in relation to the moisture condensing continuously on the condensation surface, until the target value of the humidity is reached if the measured actual value is less than the target value (the feeding of thermal energy to the liquid in the container has the effect that more liquid evaporates than condenses on the heat exchange body), or no liquid evaporates, or liquid evaporates, to a small extent in relation to the moisture condensing continuously on the condensation surface, until the target value of the humidity is reached if the measured actual value is greater than the target value (the restriction or interruption of the feeding of thermal energy to the liquid in the container has the effect that no liquid evaporates or less liquid evaporates than condenses on the heat exchange body).

An incubator with automatic fill level monitoring of the liquid container for holding the liquid to be evaporated is distinguished by the fact that a fill level sensor for the liquid is arranged in the container, a liquid feed which is connected to a liquid supply opens into the container, and regulation for the fill level monitoring is set up such that, in the case of a drop below a lower limit value, measured by the fill level sensor, for the fill level, the liquid in the container is automatically replenished via the liquid feed.

The incubator according to the invention may be used as an incubation cabinet or as a shaking incubator. For the use as a shaking incubator, the incubator additionally has a shaking device, arranged in the inner chamber, for vessels with media to be cultivated. The shaking device is set up in particular for holding microtiter plates for holding the media to be cultivated. In biotechnical processes, the desired reduction in the evaporation is achieved by the humidity regulation according to the invention which constantly keeps the humidity at a previously selected target value.

BRIEF DESCRIPTION OF THE DRAWINGS

The invention will be discussed in more detail below on the basis of the exemplary embodiments. In the figures.

DETAILED DESCRIPTION OF THE PREFERRED EMBODIMENTS

Figure 1:
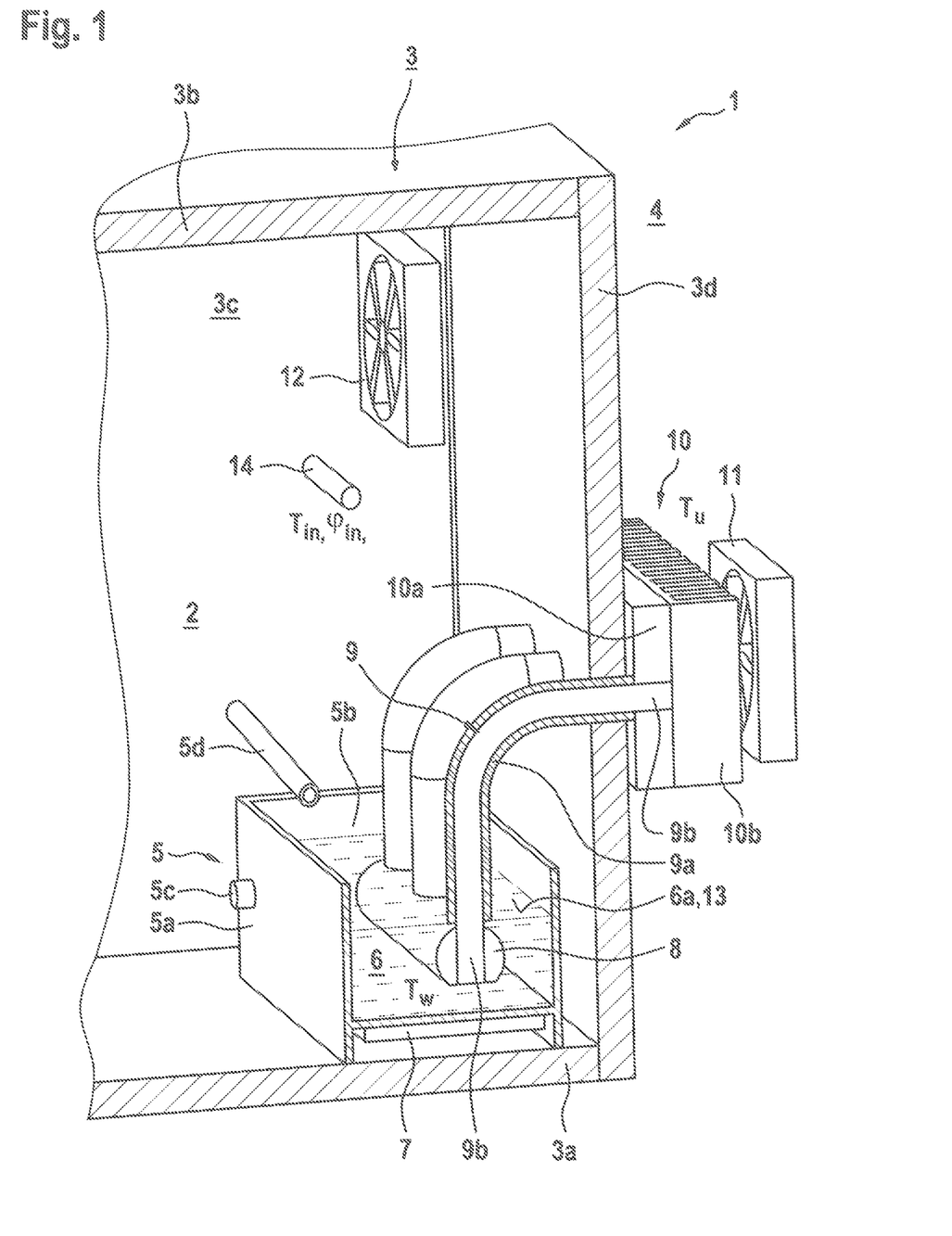
FIG. 1 is a partial sectional view of a first exemplary embodiment of an incubator according to the present invention.
Figure 1A:
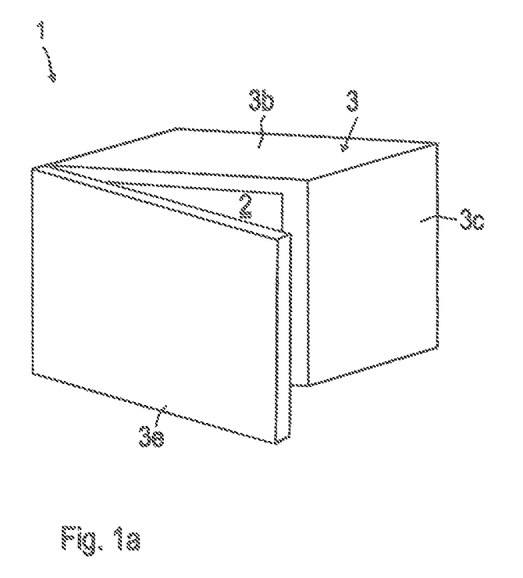
FIG. 1A is a perspective view of the incubator of FIG. 1.

As shown in FIGS. 1 and 1A, an incubator (1) with regulated humidification and temperature control of a gas mixture in an inner chamber (2) which is surrounded by a housing (3) which has a bottom (3a), a top (3b), two side walls (3c), a rear wall (3d) and a closable opening (3e), in particular in the form of a door, opposite the rear wall (3d).

The inner chamber (2) is sealed off from the surroundings (4) by the housing (3), with the result that a gas mixture in the inner chamber (2) can have not only a different composition in relation to the gas mixture in the surroundings but also a different temperature and humidity. For cultivations, temperatures in the inner chamber (2) in a range of approximately 32-37 degrees Celsius and humidity values in the range of 70-90% are required.

To reduce the heat transfer through the walls of the housing, the walls are formed as three-layer composite structures of sandwich construction. The two load-bearing covering skins consist of stainless steel. A support core composed of heat-insulating material, in particular PU foam, is situated therebetween.

To control the temperature of the gas mixture in the inner chamber (2) to an inner chamber temperature $T_{in}$, the incubator (1) has an incubator heater which, for the purpose of clarity, is not shown in FIG. 1. The incubator heater may be integrated directly into the plates which delimit the housing (3). This ensures uniform heating of the inner chamber. Furthermore, it is expedient to also provide the door of the housing (3) with a heating element, so that condensation of moisture on the door, which has a glass window multiple times, due to formation of a cold bridge is avoided. The incubator heater is connected to a regulator which keeps the inner chamber temperature $T_{in}$ at a constant level in the aforementioned region.

A humidification device (5) for evaporating a liquid is arranged on the bottom (3a) of the incubator (1). Evaporation of the liquid results in the humidity (φin of the gas mixture being increased. The humidity device (5) comprises a container (5a) for holding the liquid to be evaporated, an opening (5b) which exposes the liquid surface (6a), and a heater (7), in particular in the form of a heating mat, which is arranged on the bottom of the container (5a) and which serves for feeding thermal energy into the liquid (6). A fill level sensor (5c) which monitors the liquid level in the container (5a) is arranged on a side wall of the container (5a). A liquid feed (5d) which is connected to a liquid supply (not illustrated) through the side wall (3c) opens into the container (5a). Regulation of the fill level monitoring is set up such that, in the case of a drop below a lower limit value, measured by the fill level sensor (5c), for the fill level, the liquid in the container (5) is automatically replenished via the liquid feed (5d). This ensures that, even in the case of long-lasting cultivations, liquid is contained in the container (5), in a manner which is always sufficient, to ensure the humidity regulation in the inner chamber (2) of the incubator (1).

A heat exchange body (8) which is connected in a heat-conducting manner to three heat conductors (9) designed as heat pipes dips into the liquid (6). The heat-conducting connection is achieved by direct coupling of the heat conductors (9), which consist of material with good heat conductivity, to the heat exchange body (8) in that the ends (9b) of the heat conductors (9) engage in corresponding openings of the heat exchange body (8) in a form-fitting manner. In order to reduce the heat transfer resistance, heat-conducting paste or heat-conducting adhesive film may be used between the ends (9b) and the openings. Moreover, the heat conductors (9) may be soldered on.

The heat conductors (9) extend from the heat exchange body (8) in the direction of the rear wall (3d) to a cooling body (10) arranged outside the housing (3). Here, the heat conductors (9) extend through openings in the rear wall (3d) of the housing. Each of the three heat conductors (9) has heat insulation (9a) which surrounds the heat conductor (9) even in the passage opening in the rear wall (3d). The cooling body (10) comprises a solid baseplate (10a) which is screwed to the rear wall (3d). The baseplate (10a) comprises openings into which the non-heat-insulated ends (9b) of the heat conductors (9) engage in a form-fitting manner. To reduce the heat transfer resistance, heat-conducting paste or heat-conducting adhesive film may be used between the ends (9b) and the openings. Moreover, the heat conductors (9) may be soldered on. Lamellar cooling plates (10b) for enlarging the surface of the cooling body (10) extend at right angles to the rear wall (3d) from the baseplate (10a).

The legs of a U-shaped cover plate (not illustrated for the purpose of clarity) are screwed on the vertical, narrow side surfaces of the baseplate (10a). The web of the U-shaped cover plate, which web connects the legs, serves for the mounting of an axial fan (11) whose axis of rotation is perpendicular to the rear wall (3d).

Arranged in the inner chamber (2) of the incubator (1) close to the top (3b) is a further fan (12) which serves for ensuring sufficient mixing of the gas mixture in the inner chamber (2) such that the temperature and humidity in the entire inner chamber is homogeneous.

The method for the regulated humidification and temperature control of the gas mixture in the inner chamber (2) will be discussed in more detail below:

For the carrying out of a cultivation process, the temperature of the gas mixture in the inner chamber is controlled to a typical inner chamber temperature in the range of 32-37 degrees Celsius, the so-called cultivation temperature, and the gas mixture is kept substantially constantly at this temperature. The ambient temperature in the laboratory is for example between 20 and 25 degrees Celsius. As a result of the temperature difference between the inner chamber temperature and the ambient temperature, the liquid (6) in the container (5) is cooled by the continuous transfer of heat to the cooling body (10) arranged outside the housing by the heat conductors (9), with the result that, without action of the heater (7), the liquid (6) has a lower temperature than the inner chamber temperature $T_{in}$ of the gas mixture. Evaporation of liquid from the container (5a) is avoided because of the lower temperature, and, on the liquid surface (6a), the moisture of the gas mixture condenses directly into the container (5a). This results in the relative humidity of the gas mixture in the inner chamber being reduced. The continuous transfer of heat from the liquid surface (6a), which at the same time forms the condensation surface (13), to the cooling body (10) arranged outside the housing occurs via the heat exchange body (8) which is arranged beneath the condensation surface/liquid surface (6a) and which is connected in a heat-conducting manner to the heat conductors (9).

To increase the humidity of the gas mixture in the inner chamber (2), the liquid (6) in the container is heated by the heater (7) until liquid evaporates. The evaporative capacity is regulated with the aid of the capacity-controllable heater (7). The regulation is realized such that no moisture condenses on the liquid surface (6a), and liquid evaporates from the container (5a), until the target value of the humidity $\varphi_{soll}$ is reached if the measured actual value of the humidity $\varphi_{in}$ is less than the target value $\varphi_{soll}$. However, if the measured actual value $\varphi_{in}$ is greater than the target value $\varphi_{soll}$, for the purpose of reduction, moisture is condensed on the same liquid surface (6a) until the target value $\varphi_{soll}$ is reached. Here, the measurement of the actual value of the humidity $\varphi_{in}$ is realized by a humidity sensor (14) arranged in the inner chamber (2).

Figure 2:
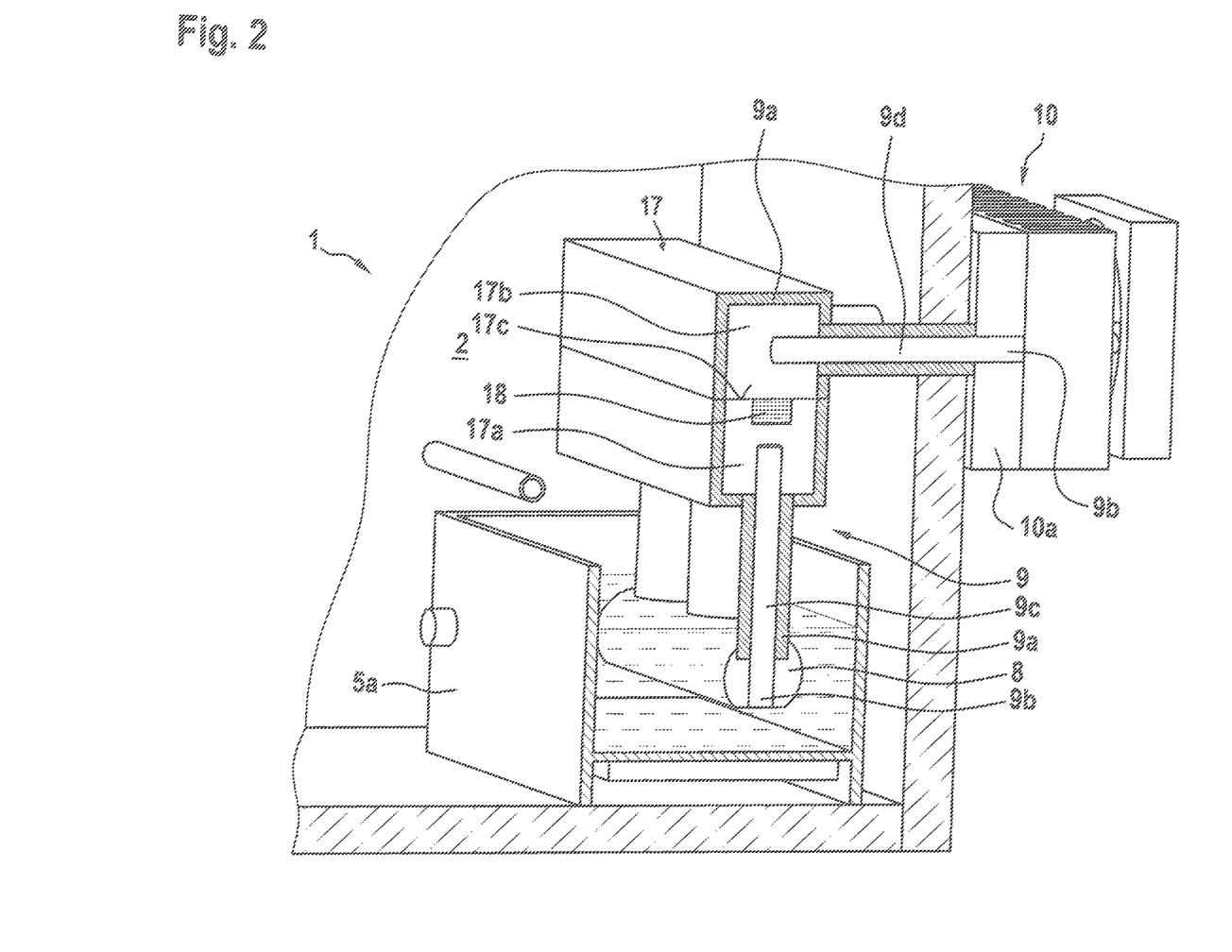
FIG. 2 is a sectional view of a further embodiment of the incubator according to the present invention.

The exemplary embodiment according to FIG. 2 substantially corresponds to the exemplary embodiment according to FIG. 1. In this respect, corresponding reference signs are used, and reference is made to the explanations regarding FIG. 1. However, a difference in relation to the exemplary embodiment according to FIG. 1 is that that section of each heat conductor (9) which runs in the inner chamber (2) consists of two sections (9c, 9d) which are releasably connected to one another in a heat-conducting manner with the aid of a connecting component (17). The connecting component (17) comprises a first cuboidal constituent part (17a) and a second cuboidal constituent part (17b). The first and second constituent parts (17a, 17b) abut against one another in a flush manner at a boundary surface (17c) and consist of a ferromagnetic material with good heat conductivity. At the boundary surface (17c), at least one permanent magnet (18) is arranged in the first constituent part (17a) and attracts the second constituent part (17b).

The first section (9c) of each of the three heat conductors (9) extends in a rectilinear manner from the heat exchange body (8) as far as the first constituent part (17a) of the connecting component (17). The second section (9d) of each heat conductor (9) extends from the second constituent part (17b) of the connecting component (17) to the baseplate (10a) of the cooling body (10). The ends of the first section (9c) of each heat conductor (9) engage into corresponding openings of the first constituent part (17a) of the connecting component (17) and of the heat exchange body (8). The ends of the second section (9d) of each heat conductor engage into corresponding openings of the second constituent part (17b) of the connecting component (17) and of the baseplate (10a) of the cooling body (10). It is further apparent that the heat insulation (9a) also completely surrounds the outwardly facing surfaces of the first and second constituent part (17a, 17b) of the connecting component to prevent condensation on the connecting component (17).

For the cleaning and removal of the container (5a) of the humidification device (5), it is possible to release the magnetic connection along the boundary surface (17c) without any problems, with the result that the heat exchange body (8) can be removed together with the sections (9c), arranged on the heat exchange body (8), of the heat conductors (9) and the first constituent part (17a) of the connecting component. Subsequently, the container (5a) can be pulled out without any problems under the second constituent part (17b) of the connecting component, which part remains in the housing (3), and the sections (9d) of the heat conductors (9).

Figure 3:
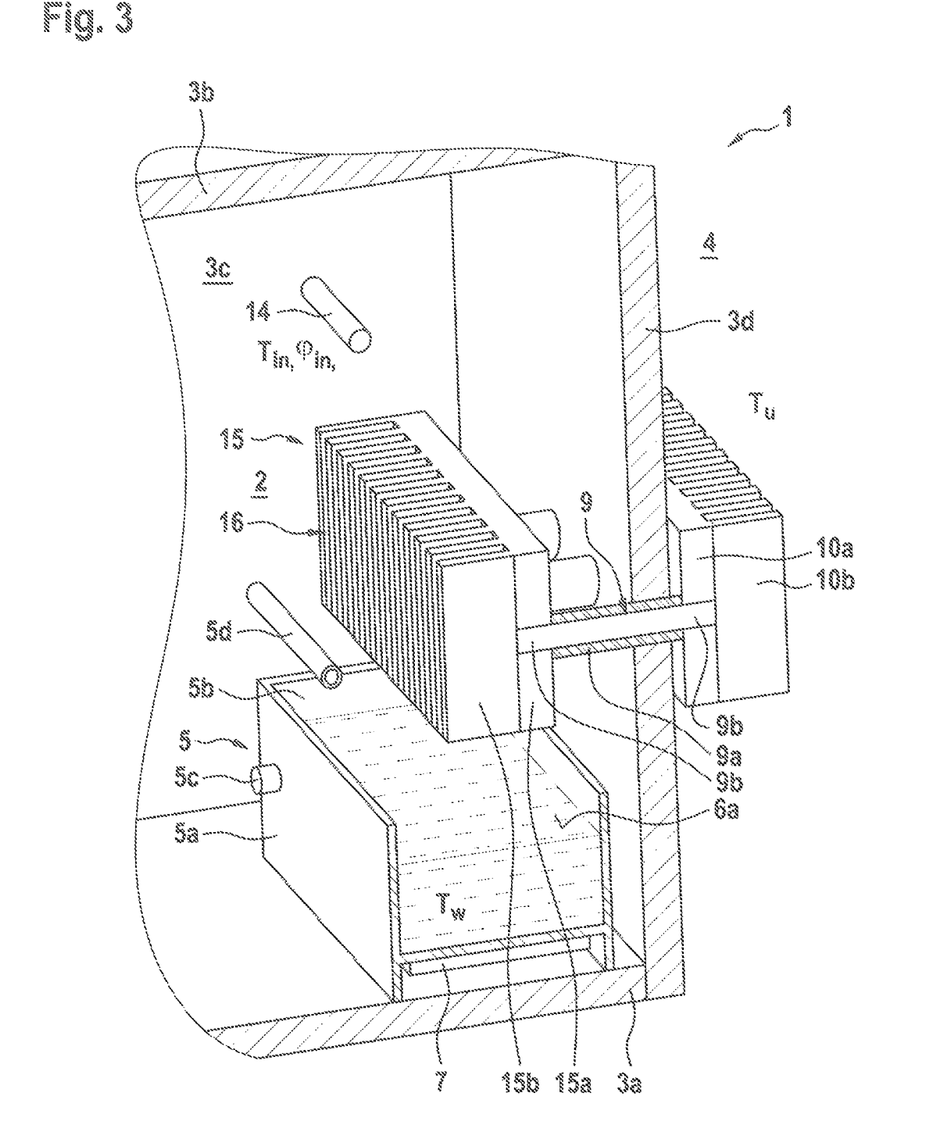
FIG. 3 is a sectional view of another exemplary embodiment of the incubator according to the present invention.

The exemplary embodiment of the incubator according to FIG. 3 partially corresponds to the exemplary embodiment according to FIG. 1. In this respect, corresponding reference signs are used, and reference is made to the explanations regarding FIG. 1. Differences arise insofar as the moisture of the gas mixture condenses not on the liquid surface (6a) but on the surface of a heat exchange body (15) which is arranged in the inner chamber (2) of the incubator (1) above the opening (5b) of the container (5a) of the humidification device (5).

The heat exchange body (15) is substantially constructed correspondingly like the cooling body (10) arranged outside the housing. It comprises a solid baseplate (15a) into which the non-heat-insulated ends (9b) of the three heat conductors (9) engage in a form-fitting manner. To reduce the heat transfer resistance, heat-conducting paste or heat-conducting adhesive film may be used between the ends (9b) and the openings. Moreover, the heat conductors may be soldered on. On the opposite site, lamellar plates (15b), which enlarge the surface for the heat transfer, extend from the baseplate (15a). The entire surface of the heat absorbing body, which surface comes into contact with the gas mixture, that is to say the surface of the plates (15b) and of the baseplate (15a), forms the condensation surface. The moisture condensing on said condensation surface drips directly into the liquid (6) because of the arrangement above the opening (5b) of the container (5a), with the result that contamination due to condensing liquid is ruled out.

By contrast with the exemplary embodiment according to FIG. 1, the heat absorbing body (15) and the cooling body (10) are connected to one another through the rear wall (3d) over a significantly shorter distance via straight heat conductors (9).

With regard to the regulation of the evaporation line by the heater (7), a difference in relation to the exemplary embodiment according to FIG. 1 arises insofar as, because of the continuous condensation on the heat exchange body (15), it is not essential for the evaporation to be completely prevented even if a reduction in the humidity of the gas mixture in the inner chamber is pursued. This makes it possible for the temporal profile of the humidity reduction to be controlled by targeted control of the evaporative capacity with simultaneous condensation on the heat exchange body (15). Specifically, the evaporative capacity is regulated in the incubator (1) according to FIG. 3 in such a way that liquid evaporates from the container (5a), to a large extent in relation to the moisture condensing continuously on the condensation surface (16) of the heat exchange body, until the target value $\varphi_{soll}$ of the humidity is reached if the measured actual value is less than the target value. In order to rapidly compensate for a regulating deviation, the humidification device (5) is preferably operated at maximum heat capacity of the heater (7).

However, if the actual value $\varphi_{in}$ of the humidity is greater than the target value, it is preferably the case that no liquid evaporates, or liquid evaporates, to a small extent in relation to the moisture condensing continuously on the condensation surface (16), until the target value of the humidity is reached. Maintenance of low evaporation can be expedient in the context of the regulation if a temporally slow reduction of the humidity is desired.

| No. | Designation |
|---|---|
| 1. | Incubator |
| 2. | Inner chamber |
| 3. | Housing |
| 3a. | Bottom |
| 3b. | Top |
| 3c. | Side wall |
| 3d. | Rear wall |
| 3e | Door |
| 4. | Surroundings |
| 5. | Humidification device |
| 5a. | Container |
| 5b. | Opening |
| 5c. | Fill level sensor |
| 5d. | Liquid feed |
| 6. | Liquid |
| 6a. | Liquid surface |
| 7. | Heater |
| 8. | Heat exchange body |
| 9. | Heat conductor |
| 9a. | Heat insulation |
| 9b. | Ends of heat conductors |
| 9c. | Sections |
| 9d. | Sections |
| 10. | Cooling body |
| 10 | Baseplate |
| 10 | Cooling plate |

-continued

| No. | Designation |
| --- | --- |
| 11. | Fan |
| 13. | Condensation surface |
| 14. | Humidity sensor |
| 15. | Heat exchange body |
| 15 | Baseplate |
| 15 | Plates |
| 16. | Condensation surface |
| 17. | Connecting component |
| 17 | First constituent part |
| 17 | Second constituent part |
| 17c | Boundary surface |
| 18. | Permanent magnet |

What is claimed is:

1. A method for regulated humidification and temperature control of a gas mixture in an inner chamber of an incubator, the inner chamber being sealed off from the surroundings by a housing, comprising the steps of
controlling a temperature of the gas mixture to an inner chamber temperature which is higher than an ambient temperature prevailing outside the incubator,
continuously transferring heat from at least one condensation surface in the inner chamber to a cooling body arranged outside the housing using at least one heat conductor,
measuring an actual value of a humidity of the gas mixture in the inner chamber,
comparing the actual value with a target value for the humidity, and
regulating the actual value of the humidity based on a deviation of the actual value from the target value by at least one of evaporating a liquid in the inner chamber using a humidification device whose evaporative capacity is able to be regulated, and condensing moisture of the gas mixture on the at least one condensation surface in the inner chamber,
wherein the step of regulating the actual value of the humidity includes varying a heat transfer from the cooling body to the ambient air by varying a flow of the ambient air along heat-emitting surfaces of the cooling body by at least one cooling fan.

2. The method according to claim 1, wherein the evaporation of the liquid is realized in a heatable container which has an opening, the opening exposes the liquid surface, and the evaporative capacity of the humidification device is regulated by a heater.

3. The method according to claim 2, wherein the moisture of the gas mixture condenses on the liquid surface which forms the at least one condensation surface.

4. The method according to claim 3, wherein the at least one heat conductor is connected in a heat-conducting manner to a heat exchange body, and the heat exchange body is at least partially submerged in the liquid.

5. The method according to claim 3, wherein the step of regulating the actual value of the humidity includes
evaporating the liquid with no moisture condensing on the liquid surface, until the target value of the humidity is reached if the measured actual value is less than the target value, or
condensing moisture on the liquid surface, with no evaporation of liquid, until the target value of the humidity is reached if the measured actual value is greater than the target value.

6. The method according to claim 1, wherein the at least one condensation surface is arranged on a heat exchange body arranged in the inner chamber of the incubator, and the step of condensing moisture includes condensing moisture on the at least one condensation surface on the heat exchange body.

7. The method according to claim 6, wherein the step of regulating the actual value of the humidity includes
evaporating liquid to an extent larger in relation to the moisture condensing continuously on the condensation surface, until the target value of the humidity is reached when the measured actual value is less than the target value, and
evaporating no liquid or evaporating liquid to an extent smaller in relation to the moisture condensing continuously on the condensation surface, until the target value of the humidity is reached when the measured actual value is greater than the target value.

8. The method according to claim 1, further comprising the step of continuously circulating the gas mixture in the inner chamber.

9. The method according to claim 1, the step of controlling the temperature includes regulating the temperature of the gas mixture to a constant value in the range of 32° C.-40° C.

10. The method according to claim 9, wherein the ambient temperature lies in the range of 20° C.-25° C.

11. An incubator with regulated humidification and temperature of a gas mixture in an inner chamber which is sealed off, wherein the gas mixture has an inner chamber temperature which is higher than an ambient temperature prevailing outside the incubator, the incubator comprising:
a housing surrounding the inner chamber and having a closable opening,
a humidification device configured to evaporate a liquid with regulable evaporative capacity, and capable of increasing the humidity of the gas mixture in the inner chamber,
a condensation surface arranged in the inner chamber configured to reduce the humidity of the gas mixture by condensation,
a cooling body arranged outside the housing,
at least one heat conductor configured to transfer heat from the condensation surface to the cooling body,
at least one cooling fan mounted on the cooling body configured to produce a flow of the ambient air along heat-emitting surfaces of the cooling body, the at least one cooling fan being controllable in terms of rotational speed,
a humidity sensor measuring an actual value of the humidity of the gas mixture in the inner chamber, and
a humidity regulator configured to compare the actual value with a target value for the humidity, and for regulating the actual value of the humidity based on a deviation of the actual value from the target value by controlling the humidification device and the condensation surface, the humidity regulator controlling the rotational speed of the at least one cooling fan for regulating the actual value of the humidity.

12. The incubator according to claim 11, wherein the humidification device has a container for holding liquid to be evaporated, at least one opening exposing a liquid surface of the liquid in the container, and a heater for feeding thermal energy into the liquid.

13. The incubator according to claim 12, further comprising:
a heat exchange body at least partially submerged in the liquid, and the at least one heat conductor being connected in a heat-conducting manner to the heat exchange body, wherein the liquid surface forms the condensation surface.

14. The incubator according to claim 12, wherein a heat exchange body is arranged in the inner chamber above the container, the liquid surface of the container at least partially forms the condensation surface.

15. The incubator according to claim 14, wherein the heat exchange body is arranged above the opening of the container.

16. The incubator according to claim 12, further comprising a fill level sensor arranged on the container and measuring a fill level of the liquid, a liquid feed connectable to a liquid supply opens into the container, and wherein, in the case of a drop of the fill level below a lower limit value, measured by the fill level sensor, the liquid in the container is replenished via the liquid feed.

17. The incubator according to claim 11, wherein a section of each of the at least one heat conductor situated in the inner chamber consists of multiple constituent parts which are releasably connected to one another.

18. The incubator according to claim 17, wherein the section of the each of the at least one heat conductor includes a first constituent part and a second constituent part releasably connected to one another by a magnetic connection.

19. The incubator according to claim 18, wherein
the first constituent part of the each of the at least one heat conductor is connected in a heat-conducting manner to a first part of a heat-conducting connecting component,
the second constituent part of the each of the at least one heat conductor is connected in a heat-conducting manner to a second part of the connecting component, and
the first part and second part of the connecting component have a boundary surface at which the magnetic connection is active.

20. The incubator according to claim 11, wherein each of the at least one heat conductor is a heat pipe.

21. The incubator according to claim 11, wherein a heat insulation is arranged on the each of the at least one heat conductor.

22. The incubator according to claim 11, wherein the humidity regulator is configured to, when the humidity is increased, switched off or operate each of the at least one cooling fan at a lower rotational speed than when the humidity is reduced.

23. The incubator according to claim 11, wherein at least one circulating fan is arranged in the inner chamber and configured to circulate the gas mixture in the inner chamber.

* * * * *